United States Patent [19]

Patel et al.

[11] Patent Number: 4,719,110
[45] Date of Patent: Jan. 12, 1988

[54] BORON-CONTAINING WOOD PRESERVATIVES

[75] Inventors: Keshav P. Patel, Oklahoma City; William C. Laughlin, Edmond; Roger A. Baldwin, Oklahoma City, all of Okla.

[73] Assignee: Kerr-McGee Chemical Corporation, Oklahoma City, Okla.

[21] Appl. No.: 769,279

[22] Filed: Aug. 26, 1985

[51] Int. Cl.$^4$ .............................................. A01N 59/14
[52] U.S. Cl. ..................................................... 424/148
[58] Field of Search ........................................ 424/148

[56] References Cited

U.S. PATENT DOCUMENTS 4,173,666 11/1979 Quinto .................................. 427/427
4,400,298 8/1983 Boocock et al. ..................... 424/148

OTHER PUBLICATIONS

The Merck Index, 10th Edition (1983) pp. 185 and 1231.

*Primary Examiner*—Leonard Schenkman
*Assistant Examiner*—Joseph A. Lipovsky
*Attorney, Agent, or Firm*—William G. Addison; John P. Ward

[57] ABSTRACT

The present invention provides for boron-containing wood preserving solutions and a method for their preparation. The wood preserving solutions of the invention are noncrystallizable at ambient temperatures and are prepared from a dispersion of a particulated sodium tetraborate, phosphoric acid and water by heating the dispersion at elevated temperatures and for a period of time sufficient to provide a clear solution. The particulated sodium tetraborate and phosphoric are present in the dispersion in a specific molar ratio of 5:3, said ratio being critical to achieving the noncrystallizable characteristic of the wood preserving solutions of the invention.

9 Claims, No Drawings

BORON-CONTAINING WOOD PRESERVATIVES

FIELD OF THE INVENTION

This invention relates to aqueous wood preserving solutions useful in the treatment of unseasoned woods, particularly by dip-diffusion processes. More particularly, this invention relates to aqueous sodium borate solutions and to a method for their preparation. The aqueous sodium borate solutions of this invention are characterized by their noncrystallizable nature over a wide range of concentrations at ambient temperatures.

BACKGROUND OF THE INVENTION

The use of boric acid and boron compounds such as borax and polyborates for the treatment of unseasoned wood is well known. For example, in New Zealand and Australia boron compounds such as borax and polyborates which are believed to convert to boric acid in wood, are used extensively to protect wood against insect and fungi attack. In general, these boron compounds are applied by dipping unseasoned wood into a tank containing an aqueous solution thereof and then storing the dipped wood for a period sufficient to allow diffusion of the boron compound into the wood. The solution is maintained in the dip tank at elevated temperatures and under constant agitation to prevent the boron compound from recrystallizing and settling out of the solution.

As can be implied from the above description of the use of borax and polyborates in the treatment of unseasoned woods, one problem associated with such use is the limited solubility of these boron compounds in water. Thus, when utilizing aqueous solutions of these boron compounds for dip-diffusion treatment of unseasoned woods it is necessary to maintain such aqueous solutions in the dip tank at elevated temperatures and under constant agitation. However, even under these conditions it is not possible to employ high concentrated solutions of these boron compounds and as a result, the amount of such compounds which can be dissolved in water and made available for diffusion into the wood during storage is severely limited. Thus, a need exists for new and improved boron compounds for use in dip-diffusion treatments for unseasoned woods and particularly for boron compounds which have a greater solubility in water at ambient temperatures than borax or the various known polyborates that have been employed.

DETAILED DESCRIPTION OF THE INVENTION

In accordance with the present invention, it now has been discovered that aqueous borate solutions can be prepared which are noncrystallizable at ambient temperatures. More particularly, it was discovered that the aqueous borate solutions of the present invention were not only noncrystallizable at ambient temperatures but also noncrystallizable over a wide range of borate concentrations. Such discovery was totally unexpected in view of the relatively low water solubility of such known boron compounds as borax (i.e., sodium tetraborate decahydrate), ammonium pentaborate, sodium pentaborate, sodium octaborate and the like.

The aqueous borate solutions of the present invention comprise solutions containing sodium borate concentrations, expressed as sodium tetraborate equivalent, ranging up to about 41 weight percent. The solutions of the present invention are prepared by first forming a dispersion comprised of particulated sodium tetraborate (either hydrated or anhydrous) as a disperse phase and phosphoric acid and water as a continuous phase. The prepared dispersion then is heated at temperatures ranging from about 70° C. up to about the atmospheric boiling point of the dispersion with temperatures ranging from about 80° C. to about 90° C. being preferred. In an alternative embodiment, the phosphoric acid and water, which form the continuous phase, first can be heated to temperatures ranging from about 70° C. to about 75° C. after which the particulated sodium tetraborate then is added with continuous agitation and the temperature of the dispersion raised to a level as disclosed hereinabove. The heating of the dispersion is continued until dissolution of the particulated sodium tetraborate reactant is complete. The resulting clear solutions comprise the wood preserving solutions of the present invention and can be employed directly for the treatment of unseasoned woods by dip-diffusion techniques.

In preparing the wood preserving solutions of the present invention the molar ratio of the particulated sodium tetraborate to the phosphoric acid in the dispersion is critical to achieving final preservative solutions which are noncrystallizable at ambient temperatures. It has been found, through experimentation, that only those solutions prepared from dispersions containing the particulated sodium tetraborate and phosphoric acid reactants in a molar ratio of 5:3 will provide wood preserving solutions that are noncrystallizable at ambient temperatures. When dispersions are employed wherein the particulated sodium tetraborate and phosphoric acid are present at molar ratios other than the critical molar ratio the resulting solutions precipitate out solid crystals upon cooling to ambient temperatures.

It will be apparent that the above critical molar ratio represents the stoichiometric ratio of sodium tetraborate and phosphoric acid required to prepare sodium pentaborate ($Na_2B_{10}O_{16}$). However, the maximum solubility of sodium pentaborate at ambient temperatures (e.g., about 25° C. to about 30° C.) is only about 16.9 weight percent expressed as sodium tetraborate equivalent and this value rapidly decreases as the temperature is lowered, resulting in precipitation of this borate from solution. However, in contrast, solutions prepared from sodium tetraborates in accordance with the present invention can contain up to 41 weight percent, calculated as sodium tetraborate equivalent, of a soluble sodium borate which does not crystallize from the resulting aqueous solution even upon being cooled to below ambient temperatures. Thus, while it might be expected that by heating a dispersion of the particulated sodium tetraborate, phosphoric acid and water at a molar ratio of the borate to the acid of 5:3 would yield sodium pentaborate, the noncrystallizable nature of the solutions of the present invention suggests the presence of either a modified sodium pentaborate specie or an entirely different borate specie. In either event, it is clear that such species have a greater solubility than that of sodium pentaborate.

In preparing the wood preserving solutions of the present invention, any source of the sodium tetraborate reactant can be employed. Thus, any of sodium tetraborate decahydrate (borax or tincal), sodium tetraborate pentahydrate (or tincalconite), sodium tetraborate tetrahydrate (or kernite) as well as sodium tetraborate (anhydrous borax) can be used in preparing the wood preserving solutions of the present invention.

For illustrative purposes, the following examples are offered as representative of the preparation of the wood preserving solutions of this invention and are not intended nor are they to be construed as limiting the scope of the invention herein described.

EXAMPLE 1

Twelve grams (12 gms.) of phosphoric acid were mixed with 111 milliliters (mls.) of water in a flask and heated, with stirring, to a temperature between 70° C. and 75° C. To this heated solution then were added 77 gms. of borax (sodium tetraborate decahydrate) to form a dispersion. The molar ratio of the borax to the phosporic acid was 5:3. Heating of the dispersion was continued at a temperature between 80° C. and 90° C. for a period of time sufficient to allow complete dissolution of all solids. The resulting clear solution contained 20 weight percent of sodium borate calculated on the basis of sodium tetraborate equivalent. On cooling of the solution to room temperature (i.e., 25° C.) no crystallization of any solid material from solution occurred. The solution is useful for the dip-diffusion treatment of unseasoned wood to protect the wood against fungi decay.

EXAMPLE 2

Following the procedure of Example 1 a second solution of this invention was prepared using 14 gms. of phosphoric acid, 94 mls. of water and 92 gms. of borax. The resulting solution contained 24 weight percent of sodium borate calculated on the basis of the sodium tetraborate equivalent. No crystallization occurred upon cooling the hot solution to room temperature. This solution is useful for the dip-diffusion treatment of unseasoned wood.

EXAMPLE 3

Following the procedure of Example 1 a third solution of this invention was prepared using 19 gms. of phosphoric acid, 58 mls. of water and 123 gms. of borax. The resulting solution contained 32 weight percent of sodium borate calculated on the basis of the sodium tetraborate equivalent. No crystallization of any solid was observed to occur upon cooling the solution to room temperature. This solution is useful for dip-diffusion treatment of unseasoned wood.

EXAMPLE 4

A fourth solution, illustrative of the wood preserving solutions of the present invention, was prepared following the procedures of Example 1. In this Example, 24 gms. of phosphoric acid, 22 mls. of water and 154 gms. of borax were mixed. The resulting wood preserving solution was a highly viscous syrup containing 41 weight percent of sodium borate calculated on the basis of the sodium tetraborate equivalent. On cooling this solution to room temperature no crystallization occurred.

As noted hereinabove, the molar ratio of the sodium tetraborate to the phosphoric acid employed to prepare the wood preserving solutions of this invention is critical. In each of the above examples a molar ratio of 5:3 was employed. The following comparative examples illustrate the criticality of this specific molar ratio and what happens when this ratio is not utilized.

COMPARATIVE EXAMPLE A

Following the procedure of Example 3, 10 gms. of phosphoric acid, 67 mls. of water and 123 gms. of borax were combined to provide a dispersion having a molar ratio of the borax to the acid of 5:1.6. The dispersion then was heated until all of the borax had dissolved. The calculated sodium tetraborate equivalent for the resulting hot solution is 32 weight percent. Upon cooling of the resulting hot, clear solution to room temperature solid crystals of borax reformed and settled out of solution.

COMPARATIVE EXAMPLE B

The procedure of Example 3 was followed to prepare a dispersion of 14 gms. of phosphoric acid, 63 mls. of water and 123 gms. of borax. The dispersion was heated to a temperature of between 80° C. and 90° C. for a period sufficient to effect complete dissolution of the borax. The molar ratio of borax to acid in this Comparative Example was 5:2.2. The resulting hot, clear solution contained 32 weight percent of sodium borate calculated on the basis of sodium tetraborate equivalent. Upon cooling to room temperature solid crystals of borax reformed and settled out of solution.

COMPARATIVE EXAMPLE C

Following the procedure of Example 3, 24 gms. of phosphoric acid, 53 mls. of water and 123 gms. of borax were combined to form a dispersion. The molar ratio of borax to acid in this dispersion was 5:3.8. The dispersion then was heated at a temperature between 80° C. and 90° C. and for a period sufficient to effect complete dissolution of borax. The resulting hot, clear solution contained 32 weight percent of sodium borate calculated on the basis of sodium tetraborate equivalent. Upon cooling to room temperature, crystals of sodium pentaborate formed and settled out of the solution.

From the above, it readily is apparent that the present invention provides an unexpected and nonobvious result. Furthermore, the molar ratio of the sodium tetraborate to phosphoric acid reactants employed to prepare the wood preserving solutions of this invention are critical to providing these solutions with their noncrystallizable properties at ambient temperatures.

The Table below contains data comparing the solubilities, at 30° C., of sodium tetraborate (i.e., borax) and various other borates to the solubility of the sodium borate solution of Example 4. The weight percentage, set forth in the Table, are expressed in terms of sodium tetraborate equivalent.

TABLE

| Boron Compound | Wt. % |
|---|---|
| Sodium tetraborate | 3.9 |
| Sodium pentaborate | 16.9 |
| Sodium octaborate | 25.9 |
| Example 4 | 41.0 |

It readily is apparent from the data in the above Table that the aqueous sodium borate solutions of the present invention possess a significantly greater solubility than those of the other borates listed.

While the present invention has been described in detail with respect to that which at present is considered to be the preferred embodiments thereof, it is understood that changes and modifications can be made to the process without departing from the spirit and scope of the invention as described above and as defined in the following claims.

What is claimed is:

1. Aqueous sodium borate solutions for use in treating unseasoned woods by a dip-diffusion process, wherein said sodium borate solutions are prepared by heating a dispersion comprising a disperse phase of a particulated sodium tetraborate and a continuous liquid phase of phosphoric acid and water, said particulated sodium tetraborate and said phosphoric acid being present in said dispersion in a molar ratio of said borate to said acid of 5:3, wherein said heating is carried out at a temperature ranging from about 70° C. up to about the atmospheric boiling point of said dispersion, said heating being continued for a period sufficient to effect a substantially complete reaction between said tetraborate and said acid and provide single phase liquid products comprising said aqueous sodium borate solutions and which aqueous sodium borate solutions are characterized as being noncrystallized at ambient temperatures.

2. The borate solutions of claim 1 wherein the particulated sodium tetraborate is selected from the group consisting of anhydrous sodium tetraborate, sodium tetraborate tetrahydrate, sodium tetraborate pentahydrate and sodium tetraborate decahydrate.

3. The borate solutions of claim 2 wherein the sodium tetraborate is sodium tetraborate decahydrate.

4. The borate solutions of claim 1 wherein the dispersion is heated at a temperature ranging from about 80° C. to about 90° C.

5. The borate solutions of claim 1 containing a sodium tetraborate equivalent, at ambient temperatures, ranging up to 41 weight percent.

6. A method for preparing aqueous sodium borate solutions for use in treating unseasoned woods by a dip-diffusion process, said method comprising providing a dispersion of a dispersed phase of a particulated sodium tetraborate and a continuous liquid phase of phosphoric acid and water, said particulated sodium tetraborate and said phosphoric acid being present in said dispersion in a molar ratio of the borate to the acid of 5:3 and heating said dispersion at a temperature ranging from about 70° C. up to about the atmospheric boiling point of the dispersion, said heating being continued for a period sufficient to effect a substantially complete reaction between the borate and the acid.

7. The method of claim 6 wherein the particulated sodium tetraborate is selected from the group consisting of anhydrous sodium tetraborate, sodium tetraborate tetrahydrate, sodium tetraborate pentahydrate and sodium tetraborate decahydrate.

8. The method of claim 7 wherein the sodium tetraborate is sodium tetraborate decahydrate.

9. The method of claim 6 wherein the dispersion is heated at a temperature ranging from about 80° C. to about 90° C.

* * * * *